United States Patent [19]
Wardley et al.

[11] Patent Number: 5,833,993
[45] Date of Patent: Nov. 10, 1998

[54] FELINE IMMUNODEFICIENCY VIRUS VACCINE

[75] Inventors: Richard C. Wardley, Hickory Corners; David E. Lowery, Portage, both of Mich.

[73] Assignee: Pharmacia & Upjohn Company, Kalamazoo, Mich.

[21] Appl. No.: 732,245

[22] PCT Filed: Apr. 5, 1995

[86] PCT No.: PCT/US95/03998

§ 371 Date: Oct. 25, 1996

§ 102(e) Date: Oct. 25, 1996

[87] PCT Pub. No.: WO95/30019

PCT Pub. Date: Nov. 9, 1995

Related U.S. Application Data

[63] Continuation-in-part of Ser. No. 236,429, Apr. 29, 1995, abandoned.

[51] Int. Cl.[6] .......................... A61K 39/21; A61K 39/12; C12Q 1/70; C07K 16/00
[52] U.S. Cl. ...................... 424/208.1; 424/199.1; 435/5; 435/69.7; 435/320.1; 530/388.35; 536/23.1
[58] Field of Search ............... 424/208.1, 199.1; 435/5, 69.7, 320.1; 530/388.35; 536/23.1

[56] References Cited

U.S. PATENT DOCUMENTS

| | | | |
|---|---|---|---|
| 5,037,753 | 8/1991 | Pedersen et al. | 435/235.1 |
| 5,118,602 | 6/1992 | Pedersen et al. | 435/5 |
| 5,275,813 | 1/1994 | Yamamoto et al. | 424/89 |
| 5,324,664 | 6/1994 | Nunberg et al. | 435/320.1 |

FOREIGN PATENT DOCUMENTS

| | | | |
|---|---|---|---|
| A 0 576 092 | 6/1992 | European Pat. Off. | |
| 0 576 092 A1 | 12/1993 | European Pat. Off. | C12N 15/86 |
| WO 90/13573 | 11/1990 | WIPO | C07K 13/00 |
| WO 90/15141 | 12/1990 | WIPO | C12N 15/41 |
| 92/15684 | 9/1992 | WIPO | C12N 15/49 |
| WO 93/08836 | 5/1993 | WIPO | |
| 94/02612 | 2/1994 | WIPO | C12N 15/49 |
| 94/02613 | 2/1994 | WIPO | C12N 15/49 |
| WO 94/03621 | 2/1994 | WIPO | C12N 15/86 |
| 94/06471 | 3/1994 | WIPO | A61K 39/21 |
| WO 94/06471 | 3/1994 | WIPO | |
| WO 94/06921 | 3/1994 | WIPO | |

OTHER PUBLICATIONS

E Young, et al., Vaccination of Cats with Recombinant FIV Envelope Protein, International Symposium on Feline Retrovirus Research, Research Triangle Park, North Carolina, USA, Oct. 6–9, 1993.
Morikawa et al., *Virology* (1991) 183:288.
Cole GE et al., *J. Virol.* (1990) 64:4930.
Olmsted et al., *Proc. Natl. Acad. Sci.* (1989) 86:2448.
Olmsted et al., *Proc. Natl. Acad. Sci. USA* (1989) 86:8088.
Pederson et al., *Science* (1987) 235:790.
Shelton et al., *J. Am. Anim. Hosp. Assoc.* (1989) 25:7.
Talbott et al., *Proc. Natl. Acad. Sci.* (1989) 86:5743.
Yamamoto et al., *J. Virol.* (1993) 67:601.
Yamamoto et al., *AIDS Res. Hum. Retroviruses* (1991) 7:911.
Nunberg et al., *J. Virol.* (1989) 63:3240.
Hu et al., *Science* (1992) 255:456.
Lutz et al., "Vaccination of Cats with Recombinant FIV env–gene Products," International Symposium on Feline Retrovirus Research, Research Triangle Park, North Carolina, USA, Oct. 6–9, 1993.
University of California v. Synbiotics Corp., 29 USPQ2d 2032 (D.C.S.D. Cal. 1994).
Verschoor, E.J. et al., Expression of Feline Immunodeficiency Virus gag and env Precursor Proteins in *Spodoptera frugiperda* Cells and Their Use in Immunodiagnosis, J. of Clinical Microbiology 31(9):2350–2355 (1993).
Yamamoto, J.K. et al., "Pathogenesis of experimentally induced feline immunodeficiency virus infection in cats," Amer. J. Veterinary Research 49(8):1246–1258, 1988.

*Primary Examiner*—Ponnathapura Achutamurthy
*Assistant Examiner*—Hankyel T. Park
*Attorney, Agent, or Firm*—James D. Darnley, Jr.

[57] ABSTRACT

Disclosed are vaccines containing both a DNA sequence encoding FIV gag protein and a DNA sequence encoding FIV env protein. The gag and env proteins are preferably expressed by baculovirus expression systems containing the DNA sequences encoding the FIV env and gag proteins or in feline herpes virus vectors containing the DNA sequences encoding the FIV env and gag proteins. Also disclosed are combined mucosal/parenteral, mucosal/mucosal and parenteral/parenteral inoculation methods.

11 Claims, No Drawings

FELINE IMMUNODEFICIENCY VIRUS VACCINE

This application is a the national phase of International Application No. PCT/US95/03998 filed Apr. 5, 1995, which is a continuation-in-part of U.S. application Ser. No. 08/236,429 filed 29 Apr. 1995, now abandoned.

FIELD OF THE INVENTION

The present invention relates generally to the fields of immunology and recombinant genetics. More specifically, the invention relates to a recombinant vaccine which includes both the DNA sequences encoding the viral envelope and gag proteins of feline immunodeficiency virus and methods of using vaccines based on these encoded DNA sequences.

BACKGROUND OF THE INVENTION

Feline immunodeficiency virus (FIV), formerly called feline T lymphotrophic lentivirus, was first isolated in 1986 from a large multiple cat household in Petaluma, Calif. (Pederson et al., Science (1987) 235:790). FIV has been classified as a member of the subfamily Lentiviridae in the family Retroviridae. This is the family that includes human and simian immunodeficiency viruses, equine infectious anaemia, maedi visna of sheep and caprine-arthritis encephalitis viruses (CAEV). The genome of FIV is organized like other lentiviruses with three long open reading frames corresponding to gag, pol and env (Talbott et al., Proc. Natl. Acad. Sci. (1989) 86:5743; Olmsted et al., Proc. Natl. Acad. Sci. (1989) 86:2448). The gag gene codes for the major structural components of the virus, the env gene codes for the envelope glycoprotein, and the pol gene codes for the polymerase protein.

The gag gene is expressed as a 50 kD polyprotein which is processed into three subunits: a p15 matrix protein, a p24 capsid protein, and a p10 nucleocapsid protein. The pol gene encodes three proteins: the protease, reverse transcriptase and a p14.6 protein of unknown function. Autoprocessing by the protease portion of the gene gives rise to all three proteins of the pol region. Additionally, the protease is responsible for the processing of the gag precursor. The pol gene is expressed as a gag-pol fusion protein. The envelope gene is expressed as a 160 kD glycoprotein, gp160. The antigenicity of the FIV core proteins is similar to other lentiviruses.

Surveys indicate that the median age of FIV infected cats in the general population is about 3 years, whereas the median age of clinically diseased FIV infected cats is about 10 years of age (Shelton et al., J. Am. Anim. Hosp. Assoc. (1989) 25:7). The clinical sequela of FIV infection in cats has been divided into five stages. Stage I, the primary phase, is quite variable with some animals showing degrees of fever, neutropenia, generalized lymphadenopathy, diarrhea and depression. Animals at this stage are normally not recognized by owners to be ill and the signs listed above have been variably recognized in experimental infections. Mortality is low and, despite recovery from this phase, virtually all cats become lifelong carriers. Viremia is by far and away the most consistent sign associated with this phase.

During Stage II, virus can still be found in the blood of cats and it is now that major abnormalities evolve in circulating numbers of CD4+ and CD8+ T cells. It is during Stage III that many cats are first presented to veterinarians with signs which range from vague clinical symptoms like recurrent fever, weight loss and anorexia, to animals which show obvious indications of chronic secondary or opportunistic infections which can include chronic oral cavity infections, chronic enteritis, chronic respiratory infections, chronic conjunctivitis and bacterial infections of the urinary tract and skin. Stage IV is dominated by the chronic secondary infections described in Stage III with further weight loss and hematological abnormalities. Finally, in Stage V, the health of cats declines further over a period of months to years and a few surviving animals may develop a condition analogous to human acquired immune deficiency syndrome (AIDS) with opportunistic infections at multiple body sites.

The virus replicates optimally in blood mononuclear cells and has a tropism for T lymphocytes, peritoneal macrophage, brain macrophage and astrocytes. In common with other retroviruses, the genetic material of FIV is composed of RNA and the production of a DNA copy of the viral RNA is an essential step in the replication of FIV in the host. This step requires the enzyme reverse transcriptase which is carried into the host by the invading virus. The DNA version of the viral genome is inserted into the genetic material of infected host cells in which it continues to reside as a provirus. This provirus is replicated every time the cell divides and can code for the production of new virus particles. Cells infected with FIV remain infected for the duration of their lifespan.

The virus appears to be spread by horizontal transmission, predominantly by bite wounds from an infected cat as these animals shed appreciable amounts of virus in saliva (Yamamoto et al., Am. J. Vet. Res. (1988) 8:1246). Vertical transmission has been reported, but is rare. Given this mode of transmission, it is theoretically possible to give a measure of protection with antibody.

At the present time there are no vaccines commercially available which provide protection against infection with FIV. Recent work suggests that cats immunized with whole infected cells or cell-free virus are protected against challenge and that protection correlated in large degree to the presence of serum neutralizing antibodies (Yamamoto et al., J. Virol. (1993) 67:601; Yamamoto et al., AIDS Res. Hum. Retroviruses (1991) 7:911. A disadvantage of these systems, however, is that the use of inactivated vaccines does not completely rule out iatrogenic transmission of FIV. Another disadvantage of using inactivated preparations is that they generally do not provide correct FIV antigen presentation for cytotoxic T cell development. Other investigators have focused on recombinant approaches to develop an FIV vaccine, either in the form of subunit or viral vectored vaccines. PCT patent application WO 92/15684 represents such an effort.

PCT patent application WO 92/15684 reports the cloning and expression of glycoprotein (gp) 160 envelope protein, gp120 envelope protein and p24 gag protein from FIV and suggests that these proteins are useful in the diagnosis, treatment and prevention of FIV. Specifically, it suggests using recombinant proteins from the gp160 envelope protein or the gag protein to develop vaccines in the prevention of FIV infection in cats. Abstracts of presentations made by the inventors of WO 92/15684, or their collaborators, at the International Symposium on Feline Retrovirus Research, Research Triangle Park, N.C., USA, Oct. 6–9, 1993, reveal that while their recombinant FIV env-gene product induces high ELISA antibody titers, these high titers do not correlate with virus-neutralization or with protection from FIV infection.

Thus, there remains a continuing need for a recombinant vaccine which yields a non-infectious FIV product and takes away the necessity of inactivating FIV-infected whole cell vaccines while providing good levels of protection. In addition to this prophylactic use, vaccines may also be useful for post-exposure immunotherapy. For example, current rabies vaccines are given to individuals following potential exposure to rabies viruses. Since FIV has a long period of latency between infection and disease progression, immunotherapy could also be of value in arresting the progression of FIV disease in infected cats.

We describe here the construction of recombinant baculoviruses and recombinant feline herpes viruses that express the gag and env genes of FIV. In addition, the present invention provides means for making FIV vaccines based on these recombinant viruses. The invention also includes methods of vaccinating a mammal by administration of a vaccine to both mucosal and parenteral sites in the natural viral host to achieve essentially full protection against persistent viraemia.

Information Disclosure

Cole G E et al., *J. Virol.* (1990) 64:4930, report the expression of feline leukemia virus envelope and gag proteins in recombinant feline herpesviruses.

Olmsted et al., *Proc. Natl. Acad. Sci.* (1989) 86:2448, report the molecular cloning of feline immunodeficiency virus.

Olmsted et al., *Proc. Natl. Acad. Sci. USA* (1989) 86:8088, report a nucleotide sequence analysis of feline immunodeficiency virus and discuss the genome organization and relationship of FIV to other lentiviruses.

Pederson et al., *Science* (1987) 235:790, report the isolation of a T lymphotrophic virus from domestic cats with immunodeficiency-like syndrome.

Shelton et al., *J. Am. Anim. Hosp. Assoc.* (1989) 25:7, report the prevalence of feline immunodeficiency virus and feline leukemia virus infections in pet cats.

Talbott et al., *Proc. Natl. Acad. Sci.* (1989) 86:5743, report the nucleotide sequence and genomic organization of feline immunodeficiency virus.

Yamamoto et al., *J. Virol.* (1993) 67:601, report the experimental protection against homologous and heterologous strains of feline immunodeficiency virus.

Yamamoto et al., *AIDS Res. Hum. Retroviruses* (1991) 7:911, report the experimental vaccine protection against feline immunodeficiency virus.

Nunberg et al., *J. Virol.* (1989) 63:3240, report the creation of a feline herpes virus (FHV) thymidine kinase deleted vector.

Hu et al, *Science* (1992) 255:456, report the protection of macaques against SIV infection by subunit vaccines of SIV envelope glycoprotein gp160.

Lutz et al., "Vaccination of Cats with Recombinant FIV env-gene Products," International Symposium on Feline Retrovirus Research, Research Triangle Park, N.C., USA, Oct. 6–9, 1993, report that while it is relatively easy to induce high ELISA antibody titers using recombinant env-gene products (baculovirus and *E. coli*), ELISA antibody titers do not correlate with virus-neutralization and with protection.

Morikawa et al., *Virology* (1991) 183:288, report the expression of FIV gag protein in a baculovirus expression system.

SUMMARY OF THE INVENTION

Disclosed are recombinant feline immunodeficiency virus (FIV) vaccines containing both a DNA sequence encoding FIV gag protein and a DNA sequence encoding FIV env protein. In one embodiment, the vaccines include a gene expression system for expressing FIV gag and env proteins from the DNA sequences encoding the FIV gag and env proteins. Among the gene expression systems available are the *E. coli*, yeast, chinese hamster ovary cells and baculovirus expression systems, with baculovirus being preferred. In an alternate embodiment, the vaccines include a replicating vector for expressing FIV gag and env proteins from the DNA sequences encoding FIV gag and env proteins. Among the replicating vectors available are the herpes, pox, adeno, retro and paramyxo viruses with feline herpes virus being preferred as the replicating vector. Other available replicating vectors are the salmonella bacteria. Also disclosed are combined mucosal/parenteral, mucosal/mucosal and parenteral/parenteral inoculation methods.

The present invention provides vaccines and methods of protecting animals from feline immunodeficiency virus (FIV) infection by vaccinating them with recombinant vaccines containing both a DNA sequence encoding FIV gag protein and a DNA sequence encoding FIV env protein each expressed by the baculovirus expression system. A combined parenteral/parenteral inoculation method is provided.

The present invention provides vaccines and methods of protecting animals from feline immunodeficiency virus (FIV) infection by vaccinating them with recombinant vaccines containing both a DNA sequence encoding FIV gag protein and a DNA sequence encoding FIV env protein each expressed by the baculovirus expression system in conjunction with recombinant vaccines containing both the DNA sequence encoding FIV gag protein and the DNA sequence encoding FIV env protein each expressed by feline herpes virus (FHV) vectors. A combined mucosal/parenteral inoculation method where a first inoculation via mucosal administration of the FHVFIenv and FHVFIgag vaccine, followed by a second inoculation via parenteral administration of the recombinant baculovirus vaccine is also provided.

The present invention provides vaccines and methods of protecting animals from feline immunodeficiency virus (FIV) infection by vaccinating them with recombinant vaccines containing both a DNA sequence encoding FIV gag protein and a DNA sequence encoding FIV env protein each expressed by feline herpes virus (FHV) vectors. A combined mucosal/mucosal inoculation method where a first inoculation via mucosal administration of the FHVFIenv and FHVFIgag vaccine, followed by a second inoculation via mucosal administration of the FHVFIenv and FHVFIgag vaccine is provided.

More particularly, this aspect of the invention provides a combined mucosal/parenteral inoculation where the first inoculation is nasal and the second is intramuscular.

Most particularly, the invention provides mucosal administration of gag and env protein via the FHV vector to a cat, followed by subcutaneous administration of gag and env protein produced by recombinant baculovirus.

Immunization kits suitable for use in the method of the invention are also provided.

DETAILED DESCRIPTION OF THE INVENTION

Both the FIV gag and env sequences used in the construction of recombinant baculovirus were obtained from an infectious proviral clone of feline immunodeficiency virus, FIV-14. This clone was originally derived from the wild-type Petaluma strain. The location and sequences of the genes encoding gag and env of FIV, as well as the protein sequences encoded thereby, are known and may be isolated following techniques well known in the art (see, e.g., Talbott et al., *Proc. Natl. Acad. Sci.* (1989) 86:5743; Olmsted et al., *Proc. Natl. Acad. Sci.* (1989) 86:2448). Numbering of the sequence is as described in Olmsted R A et al., *Proc. Natl. Acad. Sci. USA* (1989) 86:8088 (GenBank accession number M25381).

Alternatively, one can use these published sequences for gag and env to chemically synthesize the genes using an apparatus designed for this purpose following techniques well known in the art. Using recombinant techniques the genes encoding gag and env of FIV, or immunogenic portions thereof, have been transformed into plasmids and thus the genes can be conveniently, and in the transfer vectors of the invention preferably are, obtained from such a source. Exemplary plasmids are pVLFIgag* (encoding the gag gene) and pVLFIenv (encoding the envelope gene). General subcloning procedures were followed as described in Sambrook, et al., *Molecular Cloning: A Laboratory Manual* (2nd edition, 1989), Cold Spring Harbor Laboratory, Cold Spring Harbor, N.Y.

The baculovirus expression vector system (BEVS) is well known in the art as a convenient recombinant gene expression system which in some cases has been shown to produce large quantities of heterologous protein. Briefly, BEVS uses expression vectors to insert heterologous genes into the baculovirus genome at a location such that the gene will be expressed under the control of the baculovirus regulatory elements. The recombinant baculovirus is allowed to infect a cultured insect cell line, where the heterologous protein is expressed.

Several groups using BEVS have expressed the surface glycoproteins of two retroviruses. In addition, Morikawa et al., *Virology* (1991) 183:288–297, report the expression of FIV gag in the baculovirus system. BEVS is reviewed in detail by Luckow, V. A., Cloning and expression of heterologous genes in insect cells with baculovirus vectors, in *Recombinant DNA Technology and Applications*, Eds. C. Ho, A. Prokop, and R. Bajpai (1990) McGraw-Hill, New York, and Luckow, V. A. & Summers, M. D., *Bio/Technology* 6:47–55 (1988), which are incorporated by reference. For the construction of the recombinant baculovirus of the invention we use the method described in detail in the latter publication.

While there are a large number of baculovirus species known, the preferred virion for use in BEVS are *Autographa californica* nuclear polyhedrosis virus, also known as AcNPV or AcMNPV. AcNPV infects over 30 varieties of Lepidoptera cells, the preferred host being the *Spodoptera frugiperda* cell line Sf9.

The foreign genes to be inserted into baculovirus use plasmids which contain a cloning site flanked by baculovirus DNA. The cultured host cell is cotransfected with this plasmid and genomic wild-type baculovirus DNA, which recombines to produce a viral genome carrying the heterologous gene. The methods and conditions by which cotransfection occurs are well known in the art. Examples include calcium phosphate co-precipitation (Graham, F. L. and van der Eb, A. J., *Virology* 52:456467 (1973)), protamine (Wienhues, U., et al, *DNA (NY)* 6:81–89 (1987)), lipofectin (*Biotechniques* 11:310–312) and electroporation (Mann, S. G. and King, L. A., *J. Gen. Virology* 70:3501–3505 (1989)). We use the calcium phosphate method, outlined in more detail below, which is the preferred transfection method to produce the recombinant baculovirus of the invention.

Typically, the heterologous gene is targeted for insertion into the polyhedron gene, a gene which is not essential for replication or production of extracellular virus. This is generally accomplished by including in the plasmid transfer vector baculovirus DNA encoding the polyhedron promoter and sequences of 3' and 5' DNA flanking the polyhedron promoter. Foreign genes are then inserted into the transfer vector downstream of the promoter using recombinant DNA techniques known in the art. A wide variety of suitable transfer vectors are known and would be suitable for use in embodiments of the invention. Among these are pACYMI, pEV55, pAC373, pACRP, pEVIV, pEV51, and pVL941; the preferred vector is pVL941. Further, both the gag and env genes could be inserted into a single virus using several of the multiple cloning site vectors which are available. Examples of suitable multiple site vectors include p2XIVVI⁻X3, pXIVVI⁻, pSyn nWTVI⁻ (as described in *Gene* 100:131–137 (1991)), or pACVC2, as described in *Protein Engineering* 1:359–366 (1987).

The recombinant baculovirus of the invention can be identified by visual screening followed by DNA dot blot hybridization, cell affinity techniques, plaque hybridization, or other techniques known in the art. The recombinant baculovirus of the invention may also include proteins for which there are chromogenic and/or enzymatic substrates for ease of identification and purification. The preferred method is visual screening of recombinants since recombinants lack the occlusion bodies characteristic of wild-type baculovirus; visual screening is a technique which is well known in the art. The occlusion-lacking morpholytes are then picked and placed into a 96-well plate for DNA dot blot hybridization. This hybridization technique is well known in the art of recombinant DNA technology and requires no special mention. It is preferred to purify and more fully characterize several of the viruses corresponding to the strongest hybridization signals.

The recombinant baculovirus of the invention may be propagated in any number of continuously cultured insect cell lines, most typically *Anticarsa gemmitalis* (soybean caterpillar), *Bombyx mori* (silkworm), *Estigmene acrea* (saltmarsh caterpillar), *Heliothis virescens* (tobacco budworm), *Leucania separata*, *Lymantria dispar* (gypsy moth), *Malacasoma disstria* (forest tent caterpillar), *Mammestra brassicae* (cabbage worm), *Manduca sexta* (tobacco hornworm), *Plutella zylostella* (diamond-back moth), *Spodoptera exigua* (beet armyworm), and *Spodoptera littorlis*. The preferred insect cell line for the propagation of the recombinant baculovirus of the invention is *Spodoptera frugiperda* Sf-9. In addition to the baculovirus expression system, other gene expression systems which can be used in the present invention include *E. coli*, yeast, and CHO expression systems.

An alternative system for introducing immunogens into hosts are well-known replicating vectors such as feline herpes virus. Genes to be expressed in a feline herpes virus vector are placed under the control of a heterologous promoter and are inserted into the herpes virus genome. Typically, the gene to be expressed will be inserted into the thymidine kinase locus, allowing selection of recombinant viruses by loss of thymidine kinase function. The recombinant feline herpesvirus is then used to directly infect the animal, where replication allows expression of the inserted genes. Alternate replicating viruses which can be used include pox-, adeno-, paramyxo-, and retroviruses. In addition, salmonella bacteria can be used as replicating vectors.

The immunogen can be prepared in vaccine dose form by well-known procedures including the direct inoculation of plasmids containing DNA encoding the immunogen ("naked DNA vaccines").

A vaccine prepared utilizing the glycoproteins of the instant invention can consist of fixed host cells, a host cell extract, or a partially or completely purified FIV glycoprotein preparation from the host cells or produced by chemical synthesis. The FIV glycoprotein immunogen prepared in accordance with the present invention is preferably free of intact FIV virus. Thus, the vaccine immunogen of the invention is composed substantially entirely of the desired immunogenic FIV polypeptides displaying FIV antigenicity.

The vaccine can then be administered parenterally or mucosally. For parenteral administration, such as intramuscular or subcutaneous injection, the immunogen may be combined with a suitable carrier, for example, it may be administered in water, saline or buffered vehicles with or without various adjuvants or immunomodulating agents including aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionibacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.). Another suitable adjuvant is Freund's Incomplete Adjuvant (Difco Laboratories, Detroit, Mich.). Other vaccines may be prepared according to methods well known to those skilled in the art as set forth, for example, in I. Tizard, An Introduction to Veterinary Immunology, 2nd ed. (1982), which is incorporated herein by reference.

For parenteral administration the proportion of immunogen and adjuvant can be varied over a broad range so long as both are present in effective amounts. For example, aluminum hydroxide can be present in an amount of about 0.5% of the vaccine mixture ($Al_2O_3$ basis). On a per dose basis, and depending on the purity and immunogenicity of the antigen, the concentration of the immunogen can range from about 1.0 µg to about 100 mg per cat. The preferred concentration of immunogen and volume to be administered will vary depending on the age and weight of the host, as well as other factors known by those knowledgeable in the art of vaccination techniques. For example, in cats a preferable range is from about 10 µg to about 1.0 mg; a suitable dose size is about 0.5–5 ml, preferably about 1.0 ml. Accordingly, a dose for injection, for example, would comprise 1 ml containing 1.0 mg of immunogen in a mixture with 0.5% aluminum hydroxide. Comparable dose forms can also be prepared for parenteral administration to immature mammals, but the amount of immunogen per dose may be smaller, in kittens for example, about 0.25 to about 1.0 ml per dose.

For mucosal administration the immunogen may be combined with a suitable carrier, for example, water, saline, or buffered vehicles. In addition, various immunomodulating agents known in the art may be added to specifically enhance mucosal immune response. Such agents include cholera toxin or parts thereof, DEAE-dextran, interleukins (e.g. IL-5), LT toxin of *E. coli*, Shiga toxin, and other toxins from gram-negative organisms. Once formulated, such vaccines may be introduced at any mucosal surface, typically and most conveniently into the nares and/or oro-pharynx using devices suitable for this purpose e.g., dropwise with a small nasal cannula, by aerosolization, etc. The concentration of immunogen as well as dose size for mucosal administration is similar to that used for parenteral administration.

Vaccination can be accomplished following a two dose regime as disclosed in co-pending and similarly assigned Patent Application WO 9208427 which is herein incorporated by reference. As disclosed in WO 9208427, in a first embodiment the two dose regimen comprises a first dose administered to a mucosal membrane, as outlined above, followed by a second dose administered parenterally. Following this aspect of the invention, the second dose is administered at some time following the first, mucosal, inoculation. The time period which should lapse between the first mucosal inoculation and the second later-in-time, parenteral, inoculation depends on the age, weight, health, etc. of the host, the virus against which protection is sought, the immunogenicity of the respective vaccines, etc. It is well recognized that, under normal conditions, the mucosal administration would normally, but not always, comprise a replicating agent, i.e. live recombinant virus or bacteria, allowing antigens to gain access to the immune system. In addition, the second parenteral inoculation may consist of either a replicating or non-replicating agent. However, this protocol is not the exclusive mode of delivering an antigen as non-replicating antigens may be delivered to the mucosal immune system, e.g by microsphere encapsulation of antigens. These and other factors are well known in the art and the determination of the weight and relative importance of any of these factors is within the routine consideration of one skilled in the art.

The dual procedure is effective against viruses which show a compartmentalized immunogenic response i.e., viruses which gain entry into the host via a mucosal site but which also replicate systemically. The dual procedure is also effective against organisms, such as feline immunodeficiency virus, which replicate predominantly at either the mucosal site or the parenteral site.

This dual dose regime of the invention may also be accomplished by administering the two vaccine components simultaneously at their appropriate sites. Administration to both sites at precisely the simultaneous time is recognized by those skilled in the art to be unlikely and, thus, the time period for simultaneous administration includes the delay which may be experienced as, for example, the host is prepared for the second dose, the second dose is prepared for administration, the host is observed for signs of distress after the administration of the first dose, etc. Thus, when following the simultaneous administration method of the invention, a cat, for example, would receive a suitable dose of an appropriate vaccine formulation intranasally and\or orally and simultaneous intramuscular vaccination with an appropriate vaccine.

When vaccines are administered following the dual procedures of the invention, the vaccines may contain the same immunogenic component manufactured or presented in the same or different vector or formulated in the same or different vehicle. It is believed that a simultaneous dual administration as just described provides stimulation to both immunogenic compartments and thus diminishes the need for the second, later-in-time, dose.

In a second embodiment, vaccination with the FIV vaccines of the invention may also be accomplished following traditional regimes. Typically, a first dose is administered at a parenteral site or, more rarely in the case of some vaccines, at a mucosal site. The choice of site of first inoculation depends on the animal to be treated as well as the availability and suitability of the vaccine for that site. Following a suitable period of time, a second dose is administered. Traditionally, the second dose is administered at the same site as the first, i.e., if the first is mucosal the second is mucosal. The decision as to which site is appropriate for initial administration, the need for and the period of time prior to a second dose, the dose to be given, etc., are all factors known and understood by one skilled in the art of mammalian vaccination.

For example when vaccinating cats, the first dose can be given at 6–10 weeks of age. The second dose of the vaccine then should be administered some weeks after the first dose, for example, about 2 to 4 weeks later. Alternatively, the vaccine can be administered as a single 1 ml dose, for example, at about 6–10 weeks of age. However, a two dose regimen is considered preferable for the most effective immunization of the cat. Annual revaccination is recommended. Adults may be revaccinated at any time. Kittens born to unvaccinated adults may be vaccinated at about 3–10 days, again at 4–6 months and yearly thereafter.

The FIV vaccines of the invention, as well as known vaccines, when administered following traditional techniques or when administered following the dual method of co-pending Patent Application WO 9208427, may be combined with other vaccines for other diseases to produce multivalent vaccines. In addition, the vaccines of the invention, as well as known vaccines when administered following traditional techniques or when administered following the dual method of the invention, may also be combined with other medicaments, for example, antibiotics.

A "virus-like particle" is a particle produced by baculovirus infected insect cells which resembles an immature FIV particle in density (upon chromatography) and in size, shape, and ring structure (upon EM analysis).

The molecular biological, virological, and cell culture techniques described in the construction of both the recombinant baculoviruses and the recombinant feline herpes viruses expressing feline immunodeficiency antigens are within the skill of the art. Literature that describes these techniques would include Sambrook, et al., *Molecular Cloning: A Laboratory Manual*, Cold Spring Harbor Laboratory, Cold Spring Harbor, N.Y. (2nd edition, 1989); Ausubel, et al., *Current Protocols in Molecular Biology* (1987); O'Reilly, et al., *Baculovirus Expression Vectors: A Laboratory Manual* (1992); *Practical Molecular Virology* (Collins, ed., 1991); *Culture of Animal Cells: A Manual of Basic Technique* (Freshney, ed., 2nd edition, 1989); J. Miller, *Experiments in Molecular Genetics*, Cold Spring Harbor Laboratory, Cold Spring Harbor, N.Y. (1972); D. A. Morrison, *Transformation and Preservation of Competent Bacterial Cells by Freezing*, Methods Enzymol. 68:326–331 (1979); J. Perbal, *A Practical Guide to Molecular Cloning*, John Wiley & Sons (1984), and M. D. Summers and G. E. Smith, Texas Agricultural Experimental Bulletin No. 1555 (1987), all of which are incorporated by reference. Except where noted, all restriction enzymes, chemicals, and materials, or their equivalents, are readily available from commercial vendors. Endonuclease restriction follows manufacturer recommendations.

Without further elaboration, it is believed that one skilled in the art can, using the preceding description, practice the present invention to its fullest extent. The following detailed examples describe how to construct the various recombinant vaccines of the invention and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Materials and Methods

Cells, Viruses, and Plasmids

The parent baculovirus *Autographica californica* nuclear polyhedrosis virus (AcNPV), E2 strain, is obtained from Max Summers (Texas A & M University). The *Spodoptera frugiperda* cell line, Sf-9, is obtained from the American Type Culture Collection (CRL 1711). Plasmid pSP72 was obtained from Promega Biotec. Plasmid p3CL-DHFR was obtained from Fred Homa (The Upjohn Company). Plasmid pGC113 was obtained from Jack Nunberg and is described by Nunberg et al., *J. Virol.* (1989) 63:3240.

Plasmid p3CL-DHFR is a pUC18-based vector constructed for the expression of heterologous genes in eucaryotic cells. It uses the human cytomegalovirus (CMV) immediate promoter and leader (sequences–1140 to+74 relative to the start site of transcription) to drive transcription. A 550 base pair BamHI-BglII fragment containing bovine growth hormone sequences is used to supply the polyadenylation functions. The vector contains unique HindIII and SalI sites between the CMV promoter and bGH polyadenylation sequences for insertion of foreign genes.

Cell line FIV-14 was derived from the wild type Petaluma strain (Olmsted et al., *Proc. Natl. Acad. Sci.* (USA) 86:8088 (1989). The cells, parent viruses, and recombinant viruses are propagated by methods described in detail in Texas Agricultural Experimental Bulletin No. 1555 (1987).

Plasmid pVL941 is described by Luckow, V. E. and M. D. Summers, *Virology* 170:31–39 (1989).

Animals

Eighteen specific pathogen-free cats of approximately 12 weeks of age are used in all experiments. Animals are housed in a containment facility either in three groups of six animals each and were fed cat food and water ad libitum.

Western Blot Analysis

For western blot analysis, aliquots from each fraction of the gradients are separated using standard SDS PAGE. Following electrophoresis, proteins are electroblotted onto 0.22 um nitrocellulose following the procedure of Towbin, H., et al, *Proc. Natl. Acad. Sci. USA* 76:4350–4354 (1979). Unoccupied sites on the nitrocellulose are blocked by sequential incubation in PBS containing 5% non-fat dry milk (NFDM). Blots are incubated with the primary antibody and color development carried out as described by Hink, W. F., et al, *Biotechnology Progress* 7:9–14 (1991). Convalescent cat sera from experimentally FIV-infected cats was used to detect gag and env proteins on Western blots.

Preparation of Antigen For Use As Vaccine

*Spodoptera frugiperda* (Sf-9) cells in spinner flasks are infected at a cell density of $1 \times 10^6$ cells/ml at a multiplicity of infection of 5 plaque forming units (pfu)/cell. The cells are infected with the following recombinant viruses: either AcNPVFIgag* or AcNPVFIenv, or co-infected with AcNPVFgag* and AcNPVFIenv. Each culture is harvested at 66 hours post infection. Infected cells are separated from the culture medium by low speed centrifugation and stored frozen until used.

FHV recombinants expressing either FIV gag or env genes are grown in CRFK cells and harvested 3 days post-infection. After clarification to remove cell debris, supernatant fluid is titered and stored at–70° C. before use. Vaccine is formulated to contain $10^5$–$10^7$ pfu/ml.

Laboratory Assays p24 levels in cats are measured using a commercially available kit (IDEXX, Portland, Me.). p24, a group-specific antigen of FIV, is found in the blood of persistently-infected animals and hence can be used as a test for viraemia. Standardization in our laboratory indicated that within the context of known positive and negative sera, O.D. values of >0.25 are positive for viraemia.

PCR analysis of cat PBMC's was performed using two pairs of nested primers during two rounds of amplification on the thermal cycler (Perkin-Elmer Cetus, Norwalk, Conn.). The sequences of the oligonucleotide primers used in PCR and as probes for Southern blots were selected from FIV sequence data (Talbott et al., Proc. Natl. Acad. Sci. (1989) 86:5743 and Olmsted et al., Proc. Natl. Acad. Sci. (1989) 86:2448). Each round of amplification consisted of 30 cycles (Round 1: 94° C. for 1 min., 55° C. for 1.5 min., 72° C. for 2 min., 0.1 ml final cycling volume; Round 2; 94° C. for 1 min, 55° C. for 1.5 min, 72° C. for 1 min., 0.05 ml final cycling volume) where round 1 begins with genomic DNA and round 2 amplifies a 0.01 ml sample from each of the 1st round reactions.

Samples were then analyzed on a 0.9% agarose gel in TBE buffer by loading 0.05 ml of PCR round 2 product. The 804-bp DNA product was visualized by ethidium bromide staining and confirmed by Southern blot.

Following electrophoresis, transfer of DNA to nitrocellulose was done according to standard procedures (Sambrook, J., E. F. Fritsch, and T. Maniatis, (1989) Molecular Cloning: A Laboratory Manual (2nd Ed.) Cold Spring Harbor Laboratory Press, Cold Spring Harbor, N.Y.). The filter hybridization was performed using Amersham's 3'—oligolabeling system with nonradioactive detection using enhanced chemiluminescence (ECL). In the ECL reaction, horseradish peroxidase catalyzes the oxidation of luminol to detect probes which are 3'-tailed with fluorescein-dUTP and hybridized to target sequences on filters. Using the probe PJD 83: 5'- ACA TCC CCC TGA TGC TCC CAG ACC ATT ACC -3' (Talbott et al., Proc. Natl. Acad. Sci. (1989) 86:5743) [SEQ ID NO:3] at a concentration of 10 ng/ml, the membrane was hybridized at 55° C. for 2 hours.

EXAMPLE 1

Expression of FIV Gag and Env Genes

A. Cloning of Gag Gene Into Recombinant Baculovirus Expression Vector

To construct a recombinant baculovirus expressing the FIV gag gene product, the infectious proviral clone pFIV14 is digested with Hinc II and Eco RV to release a 1450 base fragment (bases 599–2049) containing the gag gene. This fragment is subcloned into the vector pSP72, digested with Sma I and dephosphorylated with calf intestinal phosphatase (CIP). The resulting intermediate plasmid (designated D4) is then digested with Bgl II and Bam HI to release the gag-containing 1450 base fragment, which is then ligated into the baculovirus expression vector pVL941 (Talbott et al., Proc. Natl. Acad. Sci. (1989) 86:5743) digested with Bam HI and dephosphorylated with calf intestinal phosphatase. The resulting vector is designated pVLFIgag.

The design of pVLFIgag results in an arrangement that allows the naturally-occurring FIV gag-pol frameshift to produce a fusion protein consisting of the FIV gag joined to the baculovirus polyhedron gene product. To eliminate this frameshift product, stop codons in all three reading frames are inserted immediately following the gag reading frame. PCR is used to produce a "replacement" 3' end for the gag gene, containing the desired stop codons. PCR primers (DAD-1: 5'- CCATGGAATTCTACCTATTTATAAATC-CAATAGTTCTCCTC-3' [SEQ ID NO:1], DAD-2: 5'-GCAATGGCCACCTTAAGCCAGAAAG-3' [SEQ ID NO:2]) are used to amplify a 389 base portion of FIV-14 containing the engineered stop codons. The PCR fragment is digested with Eco RI and the 125 base fragment containing the "replacement" gag 3' end is isolated. This fragment is then ligated into the gag-containing D4 plasmid which has been digested with Eco RI (and dephosphorylated) to remove the fragment containing the natural 3' end. The resulting plasmid, designated D4*, is then placed into pVL941 in the same manner as described above for D4 to yield the baculovirus vector pVLFIgag*. The section of the gene which is PCR-amplified is sequenced to confirm the presence of the desired stop codons.

B. Cloning of Env Gene Into Recombinant Baculovirus Expression Vector

A vector to express FIV env in baculovirus is constructed by first digesting pFIV-14 with Ase I and Nde I to remove a 2649 base fragment (bases 6257–8906) containing the FIV env gene. After treatment with Klenow to fill in the ends, the fragment is subcloned into pSP72 digested with Sma I and dephosphorylated. This intermediate plasmid, designated B1, is digested with Bam HI and Bgl II (partial digest) to remove a~2660 base fragment which is ligated into pVL941, digested with Bam HI and dephosphorylated. The resulting plasmid is designated pVLFIenv.

C. Baculovirus Transformation

Plasmids pVLFIgag* and pVLFIenv are co-transfected with the wild-type baculovirus DNA into Sf9 cells using standard baculovirus expression vector techniques (Texas Agricultural Experimental Station Bulletin No. 1555 (1987). Recombinant viruses are selected on the basis of their occlusion-negative phenotype. Five individual plaques are picked for each construct and plaque-purified five times. The viral stocks are tested for expression of the heterologous FIV gene by first infecting a 60 mm dish of Sf9 cells at an estimated multiplicity of infection of 10. At 60 hrs. post infection the conditioned media and the cells are harvested and tested for expression of FIV proteins by Western blot analysis. Serum from a cat experimentally infected with FIV is used to probe the Western blot. Positive clones producing the highest levels of protein are selected to make viral stocks.

D. FIV Env and Gag Expression (Baculovirus)

Sf9 cells growing in suspension culture are used to produce larger quantities of protein for animal experiments. Suspension cells are grown in spinner flasks in media consisting of supplemented Grace's media (Gibco BRL) containing 10% fetal calf serum. The media is also supplemented with amphotericin B (2.5 ug/ml), penicillin (10 U/ml), and streptomycin (10 ug/ml). Cells are infected at a density of $1 \times 10^6$ cells/ml with an m.o.i. of 10. Sixty-six hours post infection the cells are harvested by centrifugation. Expression is confirmed by Western blot analysis prior to use. The blot is probed with FIV-reactive antisera from an experimentally infected cat. Infected cells are stored frozen at –20° C.

E. Cloning of Gag and Env Genes Into Recombinant Feline Herpes Virus

The same FIV sequences used for expression of FIV gag and env genes in baculovirus are used to construct recombinant feline herpesviruses expressing FIV gag and env gene products.

The gene containing FIV gag coding sequences is removed from the FIV proviral clone FIV-14 by digestion with Hinc II and Eco RV. This 1450 base fragment is subcloned into the vector p3CL-DHFR which has been digested with Hind III, the ends filled in with Klenow, and dephosphorylated. The resulting plasmid, p3CLFIgag is then digested with Eco RI (partial) and Bgl II to liberate a fragment containing the entire transcription unit, which consists of the CMV immediate early promoter, the FIV gag gene, and the bovine growth hormone polyadenylation signal. This fragment is subcloned into the plasmid pGC113 (Nunberg J H et al., *J. Virol.* (1989) 63:3240) at the Hind III site (both insert and vector blunt-ended with Klenow) to give the plasmid pGCFIgag. The transcription unit is flanked by FHV thymidine kinase gene sequences to allow homologous recombination into the FHV genome, and is missing~450 bases from the middle of the thymidine kinase gene in order to attenuate the virus (absent from pGC113 as described in Nunberg J H et al., *J. Virol.* (1989) 63:3240).

A similar strategy is used to produce a transfer plasmid for expressing FIV env. The coding sequence for FIV env is removed from FIV-14 by digestion with Ase I and Nde I and subcloned into pSP72 digested with Pvu I and dephosphorylated to produce the plasmid designated F5. The env gene is removed from plasmid F5 with Hind III and Xho I and subcloned into p3CL-DHFR digested with Hind III and Sal I, yielding the plasmid p3CLFIenv. The fragment containing the CMV promoter, FIV env gene and bGH polyadenylation sequences is removed by digestion with Eco RI and Pvu II, blunt-ended with Klenow, and subcloned into the Hind III site of pGC113 (filled-in with Klenow) to give the plasmid pGCFIenv.

F. FIV Env and Gag Expression (FHV)

Recombinant FHV's expressing FIV gag or env are produced essentially as described in Nunberg J H et al., *J. Virol.* (1989) 63:3240). This involves using homologous recombination to replace the native thymidine kinase gene with the deleted thymidine kinase gene containing the FIV gene transcription unit. CRFK cells are co-transfected using a standard calcium phosphate precipitate transfection protocol with equal amounts of either pGCFIgag or PGCFIenv and purified FHV (UT88) DNA. After 100% CPE is reached (3–5 days), the resulting virus pool is serially diluted and re-plated on CRFK cells in the presence of 100 ug/ml thymidine arabinoside (araT) to select for thymidine kinase-negative viruses. Eight plaques are picked from each transfection, amplified on CRFK cells, and viral DNA is prepared. The viral DNA is analyzed by restriction digest with Eco RI and subsequent Southern blot analysis using both FIV-specific and tk-specific DNA probes. DNA-positive clones are analyzed for expression of FIV proteins by Western blot analysis of infected cell lysates.

EXAMPLE 2

Vaccination and Challenge Experiments

Eighteen specific pathogen free cats of approximately 12 weeks of age are used in this experiment. Animals are housed in containment facilities in three groups of six animals each and fed dried cat food and water ad.libitum.

A. Vaccination Groups

1. Combined Mucosal/Parenteral Vaccination

After a period of acclimation, animals in Group I (n=6) are intranasally inoculated with 0.5 ml. of FHVFIgag and 0.5 ml. of FHVFIenv (1 ml total). This is accomplished by using a syringe to which a small nasal canula has been attached. Animals are gently restrained and approximately 0.25 ml is dropped into each nostril and 0.5 ml placed towards the back of the oropharynx. Each separate preparation contains $10^{6.5}$ $TCID_{50}$ per ml. Approximately three weeks later animals are revaccinated subcutaneously with $10^{6.5}$ Sf9 cells, suspended in saline, which 72 hours previously had been infected, at an MOI of 1, with recombinant baculoviruses with FIV gag and env insertions.

2. Combined Parenteral/Parenteral Vaccination

Animals in Group II (n=6) are inoculated subcutaneously with $10^{6.5}$ Sf9 cells suspended in saline, which 72 hours previously had been inoculated, at an MOI of 1, with recombinant baculoviruses with FIV gag and env insertions. Approximately three weeks later these animals are revaccinated with a similar recombinant baculovirus preparation.

3. Combined Mucosal/Mucosal Vaccination

After a period of acclimation, animals are intranasally inoculated with 0.5 ml. of FHVFIgag and 0.5 ml. of FHVFIenv (1 ml total). This is accomplished by using a syringe to which a small nasal canula has been attached. Animals are gently restrained and approximately 0.25 ml are dropped into each nostril and 0.5 ml placed towards the back of the oropharynx. Each separate preparation contains $10^{6.5}$ $TCID_{50}$ per ml. Approximately three weeks later animals are revaccinated in a similar manner with the identical dose.

4. Control

Animals in Group III (n=6) are left as unvaccinated controls.

B. Challenge

Approximately two weeks after the last vaccination, animals in each of the three groups are challenged intravenously with a one ml dose of a $10^{-3}$ dilution of a cloned viral stock of the Petaluma isolate of FIV. There is no evidence of immunosuppression. Titration of this stock in susceptible cats using a similar route and inoculation amount has shown it to have a titer of 10000 ID50s.

Blood taken from these cats at 24 weeks post challenge is separated on Ficol gradients to enrich for mononuclear cells. These cells are cultured at $10^5$ per ml in RPMI 1640 with 10% fetal calf serum in the presence of 2 $\mu$g Con A and 100 IU of recombinant human IL-2 per ml. After three days cells are spun down and resuspended in RPMI 1640 with 10% fetal calf serum and 100 IU of recombinant human IL-2 per ml. After 21 days in culture, cells are prepared for PCR analysis.

Cat peripheral blood mononuclear cells (PBMC's) are harvested on the 21st day of culture by centrifugation at 1500×g. Cells are then washed with Hank's Balanced Salt Solution (HBSS). Genomic DNA is isolated from approximately $10^7$ cells using the Turbogen Kit (Invitrogen Corporation, San Diego, Calif.). Briefly, cells are lysed using a denaturing cationic detergent. Then detergent and denatured protein are removed via chloroform extraction. Genomic DNA is precipitated from the aqueous phase with a low salt buffer and ethanol is then dissolved in TBE buffer and stored at 4° C. until analysis by PCR (described in Laboratory Assays).

C. Results

Table 1 shows that four of six animals in the control group are viremic at 24 weeks, whereas none of the animals inoculated parenterally/parenterally or mucosally/parenterally are positive on either the ELISA antigen assay or PCR. This indicates that these vaccination schedules successfully prevent persistent viraemia with FIV. It is expected that mucosal/mucosal vaccination will achieve similar results.

EXAMPLE 4

Vaccination Kit

A kit containing the vaccines for administration and instruction on the dual mucosal/parenteral administration of vaccines, parenteral/parenteral or mucosal/mucosal administration of vaccines, as described herein, may be produced as a safe and cost efficient means of supplying a vaccine. The vaccination kit contains vaccines in single or multiple use vials, ampules, or other suitable containers. For mucosal administration the formulated vaccine may be in containers or in an aerosolized form. For parenteral use, single dose syringes containing a suitable efficacious dose for the host mammal represent an easy and rapid way in which administration is accomplished. Alternatively, the kit may contain the mucosal and parenteral vaccines in multi-use vials or other suitable containers, and may be supplied ready-to-use or require some additional preparation or mixing prior to use. An instruction sheet is included which more fully describes the included vaccine(s) to be administered and their formulation, the order and timing of inoculation, as well as additional factors of concern to the practitioner.

For cats, as an example, such a vaccination kit may contain a one ml, single dose, mucosal formulation containing FHVFIenv and FHVFIgag ($2 \times 10^5$ pfu/vaccine) to be administered 0.5 ml to each nostril. The parenteral formulation includes one ml of AcNPVenv and AcNPVgag ($2 \times 10^5$ pfu/vaccine) for intramuscular administration.

The foregoing detailed description is given for clearness of understanding only, and no unnecessary limitations should be inferred therefrom, as modifications within the scope of the invention will be obvious to those skilled in the art.

TABLE 1

FIV antigen and PCR results on 24 week samples.

| Cat number and vaccination history | Assay Result* | |
|---|---|---|
| | FIV antigen assay | PCR result on 21 day cultured PBMC |
| XXD3 CONTROL | − | − |
| XXE2 CONTROL | + | + |
| XXH3 CONTROL | + | + |
| XXA2 CONTROL | + | + |
| XXH2 CONTROL | + | + |
| XXS3 CONTROL | − | − |
| XXQ3 BACULO REC. | − | − |
| XXE3 BACULO REC. | − | − |
| XWL2 BACULO REC. | − | − |
| XXH1 BACULO REC. | ND | ND |
| XWG2 BACULO REC. | ND | ND |
| XWE3 BACULO REC. | ND | ND |
| XXL1 FHV REC. | − | − |
| XXB1 FHV REC | − | − |
| XWX3 FHV REC | ND | ND |
| XWP3 FHV REC | − | − |
| XWR2 FHV REC | − | − |
| XWR1 FHV REC | − | − |

*Antigen presence assayed on the IDEXX ELISA and PCR analysis performed according to the text. + signifies a positive result − signifies a negative result. ND = not done (cultured cells were lost due to lack of growth and were not available for testing at the end of the experiment).

We claim:

1. A recombinant feline immunodeficiency virus (FIV) feline vaccine comprising a gene expression system for expressing FIV gag and env proteins from DNA sequences encoding FIV gag and env proteins wherein said gene expression system is a baculovirus expression system.

2. A recombinant feline immunodeficiency virus (FIV) feline vaccine comprising a replicating vector for expressing FIV gag and env proteins from DNA sequences encoding FIV gag and env proteins wherein said replicating vector is selected from the group consisting of herpes, pox, adeno, retro and paramyxo viruses and salmonella bacteria.

3. A vaccine in accordance with claim 2 wherein said recombinant replicating vector is feline herpes virus.

4. A recombinant feline immunodeficiency virus (FIV) vaccine comprising a DNA sequence encoding FIV gap protein and a DNA sequence encoding FIV env protein wherein said DNA sequences encoding FIV gag and env proteins are expressed by both a gene expression system and a replicating vector and wherein said gene expression system is selected from the group consisting of *E. coli*, yeast, chinese hamster ovary cells and baculovirus and said replicating vector is selected from the group consisting of herpes, pox, adeno, retro and paramyxo viruses and salmonella bacteria.

5. A vaccine in accordance with claim 4 wherein said gene expression system is a baculovirus expression system and said replicating vector is feline herpes virus.

6. A method of vaccinating a cat against feline immunodeficiency virus (FIV) comprising:

administering to the cat a first dose of a recombinant feline immunodeficiency virus (FIV) vaccine comprising a DNA sequence encoding FIV gag protein and a DNA sequence encoding FIV env protein followed by a second dose of said vaccine wherein said first and second doses of said vaccine are administered parenterally.

7. A method in accordance with claim 6 wherein said first and second doses of said vaccine comprise DNA sequences encoding FIV gag and env proteins expressed by a baculovirus expression system.

8. A method of vaccinating a cat against feline immunodeficiency virus (FIV) comprising:

administering to the cat a first dose of a recombinant feline immunodeficiency virus (FIV) vaccine comprising a DNA sequence encoding FIV gag protein and a DNA sequence encoding FIV env protein followed by a second dose of said vaccine wherein said first dose of said vaccine is administered mucosally and said second dose of said vaccine is administered parenterally.

9. A method in accordance with claim 8 wherein said first dose of said vaccine comprises DNA sequences encoding FIV gag and env proteins expressed by FHVFIenv and FHVFIgag and said second dose of said vaccine comprises DNA sequences encoding FIV gag and env proteins expressed by a baculovirus expression system.

10. A feline vaccination kit comprising:

(a) a recombinant vaccine comprising DNA sequences encoding both FIV gag and env proteins expressed by FHV for mucosal administration; and (b) a recombinant feline immunodeficiency virus (FIV) vaccine comprising a DNA sequence encoding FIV gag protein and a DNA sequence encoding FIV env protein expressed by a baculovirus expression system for parenteral administration.

11. A feline vaccination kit comprising a recombinant feline immunodeficiency virus (FIV) vaccine comprising a DNA sequence encoding FIV gag protein and a DNA sequence encoding FIV env protein expressed by a baculovirus expression system for parenteral administration.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCATGGAATT CTACCTATTT ATAAATCCAA TAGTTCTCCT C        41

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCAATGGCCA CCTTAAGCCA GAAAG        25

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:3:

ACATCCCCCT GATGCTCCCA GACCATTACC                    30